United States Patent [19]

Whittle et al.

[11] 4,089,903
[45] May 16, 1978

[54] PREPARATION OF VICINAL-CHLORAMINOALKANES FROM ALPHA-OLEFINS CHLORAMINES AND ALUMINUM HALIDE CATALYSTS

[75] Inventors: Joanne R. Whittle, Nederland; Orville W. Rigdon, Groves, both of Tex.

[73] Assignee: Texaco Inc., New York, N.Y.

[21] Appl. No.: 700,625

[22] Filed: Jun. 28, 1976

[51] Int. Cl.$^2$ .............................................. C07C 85/18
[52] U.S. Cl. .................... 260/583 G; 260/570.8 R; 260/570.9; 260/585 D
[58] Field of Search ........ 260/583 G, 583 NH, 585 D

[56] References Cited

PUBLICATIONS

Neale et al. (I), "J. Org. Chem.", vol. 33(9), pp. 3457–3460, (1968).
Strand et al., "J. Amer. Chem. Soc.", vol. 95(9), pp. 2977–2982, (1973).
Neale et al. (II), "J. Amer. Chem. Soc.", vol. 85(9), pp. 2666–2667, (1963).
Neale, "J. Org. Chem.", vol. 32(11), pp. 3263–3273, (1967).
Neale et al. (III), "J. Org. Chem.", vol. 32(11), pp. 3273–3284, (1967).

*Primary Examiner*—Daniel E. Wyman
*Assistant Examiner*—John J. Doll
*Attorney, Agent, or Firm*—Thomas H. Whaley; Carl G. Ries; Bernard Marlowe

[57] ABSTRACT

This invention concerns a process for preparing beta-chloraminoalkanes from alpha olefins, chloramines and aluminum halide catalysts. The products are useful as lube oil additives and for making aziridines.

5 Claims, No Drawings

PREPARATION OF VICINAL-CHLORAMINOALKANES FROM ALPHA-OLEFINS CHLORAMINES AND ALUMINUM HALIDE CATALYSTS

SUMMARY OF THE INVENTION

This invention concerns the catalyzed addition of chloramines to alpha-olefins to form chloraminoalkanes.

More particularly, this invention relates to the addition of monochloroamine and N-alkyl monochloroamines to alpha-olefins in the presence of aluminum chloride or aluminum bromide catalysts to prepare vicinal chloroaminoalkane products. These products are useful as lube oil additives and for the preparation of aziridines when treated with base.

BACKGROUND OF THE INVENTION

A considerable quantity of alpha-olefins are now available from the cracking of wax derived from petroleum processing. Inasmuch as the monofunctional alpha-olefins are relatively inexpensive a great deal of research work has been undertaken to upgrade these monofunctional substrates to higher value multifunctional products. A promising class of potential products are vicinal- chloroaminoalkanes which contain chloro and amino groups on vicinal carbon atoms in the molecule. The potential market for these di-functional products is estimated to be in the order of millions of pounds.

A useful reactant for converting alpha-olefins to vicinal chloroaminoalkanes is monochloramine ($NH_2Cl$) which can be prepared in at least two different ways published in the literature. One reported method of synthesis is the reaction of chlorine with ammonia in the gaseous state*. Another method is to react solutions of sodium hypochlorite with a solution of ammonia.** Either method is acceptable dependent upon the quantity of starting material required. The generic reaction is to react an alpha-olefin containing 4 to 20 carbon atoms with chloramines at temperatures below 0° and at atmospheric pressure in the presence of aluminum halide, preferably $AlCl_3$ to produce chloroaminoalkane isomers designated as compounds I and II.

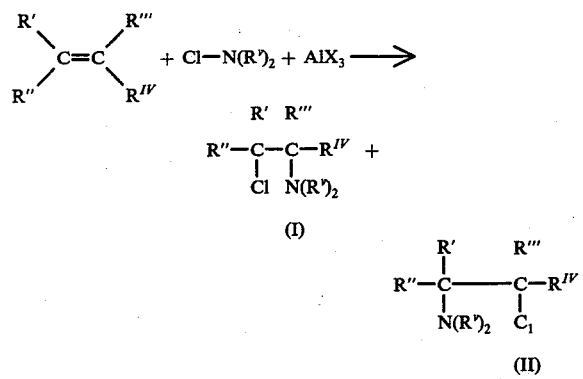

$R'$, $R''$, $R'''$, $R^{IV}$ = alkyl, aryl or hydrogen and X is chlorine or bromine, $R^v$ = H or alkyl and X is chlorine or bromine. The above chloroaminoalkane products can be converted to aziridines by the reaction of a strong base such as potassium or sodium hydroxide, preferably in the presence of lower alkanol.

*Sisler et al (JACS, 76.3906(1954)
**Coleman et al, Inorg. Syn. 1, 59(1939)

To enable the reader to more readily grasp the essence of the preferred embodiments, the following additional disclosure regarding the reaction parameters are discussed briefly. Finally these reaction parameters are followed by illustrative examples, and Tables. It should be noted that unless otherwise noted all parts and percentages are by weight and all degrees are in centigrade.

REACTION PARAMETERS

1. Effect of Catalyst to Reactant Ratio and Monochloramine Yield and Selectivity.

Experimental work shown in Table II indicates that the yield of chloroaminoalkanes increases with increasing aluminum chloride concentration with respect to both chloroamine and olefin.

2. Effect of Solvent on the Yield of Product.

The nature and quantity of the solvent also has a substantial effect on the course of the reaction. Table III shows that maximum yields are obtained using a mixed methylene chloride - diethyl ether solvent in the ratio of about 6:1.

3. Effect of Reaction Time on the Yield of Product.

As Table IV documents, a slight advantage is obtained in reaction times over an hour.

4. Reaction Temperatures.

Low reaction temperatures ranging from $-50°$ to $-10°$ C are favored for the best yields of product. However, the process is operable at temperatures ranging from $-77°$ C to $0°$ C with temperatures ranging from $-50°$ C to $-10°$ C being preferred.

5. Reaction Pressures.

Pressure is not critical to the operability of the inventive process. That is, pressures may range from atmospheric up to superatmospheric. However, inasmuch as operating at superatmospheric pressures is more costly than operating at atmospheric pressures, and offers no advantage in yield, atmospheric pressures are used.

EXAMPLE 1

ADDITION OF MONOCHLOROAMINE TO 1-DODECENE USING ALUMINUM CHLORIDE CATALYST

To an appropriate sized reactor fitted with a stirring means, heating means, cooling means, a reflux condenser and an inlet and outlet for inert gas environment, is charged a cold ($-77°$ C) solution of 0.055 moles of monochloramine [prepared by the method of Coleman and H. L. Johnson, Inorg. Syn. 1, 59 (1939)] in 250 ml of methylene chloride, followed by the addition of aluminum chloride (0.8 moles). After about 5 minutes of stirring, 0.4 moles of diethyl ether is added and finally after another 5 minutes of stirring 0.4 more moles of diethyl ether and 0.1 moles of 1-dodecene are added forming a reaction mixture. The cooled stirred reaction mixture is warmed to $-35°$ C with continuous stirring for 1½ hours. At the end of this time 80 g of a 28% aqueous HCl solution and 100–200 g of water are added to the reaction mixture with continuous stirring. This mixture is then stirred for one half-hour. The organic and water layer are separated. The organic layer is stirred with an additional 80 g portion of 28% aqueous HCl for one-half hour. The organic and water layers are separated. The water layers from the above procedure were combined and extracted with two 100 ml portions of diethylether. The ether extracts were combined with the organic layer. The organic layer was then stripped of solvent and filtered, yielding 0.024 moles of amine salt (42.9% yield based on monochloramine starting material). Using the above procedure, various reaction parameters were studied and the results are summarized in Table I.

TABLE I

| Run | 1-dodecane grams | 1-dodecane moles | NH₂Cl grams | NH₂Cl moles | AlCl₃ grams | AlCl₃ moles | SOLVENT, grams CH₂Cl₂ | SOLVENT, grams Diethyl-ether | SOLVENT, grams Total | dodecene Reaction Time Hrs. | Chloroamino-dodecene Yield % of Theory |
|---|---|---|---|---|---|---|---|---|---|---|---|
| 1 | 67.2 | 0.4 | 2.88 | 0.056 | 13.33 | 0.1 | 347 | 59 | 406 | 1.0 | 14.5 |
| 2 | 67.2 | 0.4 | 4.21 | 0.082 | 26.67 | 0.2 | 361 | 59 | 420 | 1.0 | 24.5 |
| 3 | 33.6 | 0.2 | 1.95 | 0.038 | 26.67 | 0.2 | 342 | 59 | 401 | 2.0 | 25.8 |
| 4 | 16.8 | 0.1 | 1.70 | 0.033 | 26.67 | 0.2 | 338 | 59 | 397 | 1.0 | 37.1 |
| 5 | 33.6 | 0.2 | 2.76 | 0.054 | 53.34 | 0.4 | 394 | 59 | 453 | 1.0 | 37.8 |
| 6 | 16.8 | 0.1 | 2.52 | 0.049 | 53.34 | 0.4 | 414 | 59 | 473 | 1.25 | 39.6 |
| 7 | 16.8 | 0.1 | 2.83 | 0.055 | 106.7 | 0.8 | 381 | 59 | 440 | 1.5 | 42.9 |
| 8 | 67.2 | 0.4 | 3.86 | 0.075 | 26.67 | 0.2 | 361 | 104 | 465 | 1.0 | 16.9 |
| 9 | 67.2 | 0.4 | 4.11 | 0.080 | 26.67 | 0.2 | 0 | 179 | 179 | 1.0 | 8.15 |
| 10 | 67.2 | 0.4 | 3.24 | 0.063 | 26.67 | 0.2 | 354 | 59 | 413 | 3.0 | 26.0 | a percent yield of theory = moles chloroaminodecane × 100 moles NH₂Cl charged

EXAMPLE 2

ADDITION OF N,N-DIMETHYLCHLOROAMINE TO 1-TETRADECENE USING ALUMINUM CHLORIDE CATALYST

To a reactor of the type used in Example 1 is charged a cold solution of N,N-dimethylchloramine (0.87 moles), chilled to −77° C, in 300 ml of methylene chloride, followed by aluminum chloride (0.3 moles). The mixture is stirred for 5 minutes and then diethyl ether (0.4 moles) is added. After stirring for an additional 5 minutes, an additional portion of diethyl ether (0.4 moles) and 1-tetradecene (0.3 mol) is added to the stirred solution. The chilled reaction mixture is heated to −35° C and the reaction mixture stirred for one hour. At the end of this time an 80 g portion of hydrochloric acid (28% by weight) and 100–300 g of water are added to the reaction mixture and stirred for a half hour. The organic and water layers are then separated and the organic layer is stirred for an additional half-hour with 80 g of the same strength hydrochloric acid used previously. Again the organic and water layers are separated. The organic layer is filtered to yield 0.02 mol of tetradecyl amine salt. This represents a 6.68% yield based on the amount of 1-tetradecene charged.

EXAMPLE 3

UNSUCCESSFUL ATTEMPT TO ADD MONOCHLORAMINE TO 1-DODECENE WITHOUT CATALYST AT HIGHER TEMPERATURE

In this example, using the reactor of Example 1, the uncatalyzed addition of monochloramine to 1-dodecene is attempted without the presence of anhydrous aluminum chloride, the catalyst of Example 1. A mixture of chilled monochloramine/diethyl ether solution and 1-dodecene is heated to 36° C with stirring for one hour. At the end of this time the solution is dried and stripped under vacuum leaving 35 g of residue. Analytical data show the product to be unreacted 1-dodecene. As this example demonstrates, even with much higher reaction temperatures, no product is obtained in the absence of aluminum chloride catalyst.

EXAMPLE 4

UNSUCCESSFUL ATTEMPT TO ADD MONOCHLORAMINE TO 1-DODECENE WITHOUT CATALYST AT BOTH HIGHER TEMPERATURES AND SUPERATMOSPHERIC PRESSURES

In this example, using the same type of reactor used in Example 1, the chilled 1-dodecene-diethyl ether solution and monochloroamine-ether solution of the preceding example are heated to 93° C under autogenous pressures. After 4 1.2 hours of heating the pressurized reactor is cooled, vented and worked up. Analytical data show the residue of 23 g to be unreacted 1-dodecene. Inasmuch as much more forcing reaction conditions of temperature and pressure failed to produce product, this example demonstrates that the presence of catalyst is essential.

TABLE II
EFFECT OF ALUMINUM CHLORIDE CONCENTRATION ON CHLOROAMINODODECANE YIELD [1]

| RUN NO. | MOLE RATIOS NH₂Cl | MOLE RATIOS AlCl₃ | MOLE RATIOS 1-dodecane | CHLOROAMINO-DODECANE YIELD, % OF THEORY |
|---|---|---|---|---|
| 1 | 1.0 | 1.8 | 7.1 | 14.5 |
| 2 | 1.0 | 2.4 | 4.8 | 20.8 |
| 3 | 1.0 | 5.5 | 5.5 | 25.8 |
| 4 | 1.0 | 6.2 | 3.1 | 37.5 |
| 5 | 1.0 | 7.7 | 3.8 | 37.8 |
| 6 | 1.0 | 8.3 | 1.7 | 39.6 |
| 7 | 1.0 | 14.5 | 1.8 | 42.9 |

[1]Ratio of CH₂Cl₂/diethyl ether 6–7/1 in all runs

TABLE III
EFFECT OF SOLVENT ON CHLOROAMINODODECANE YIELD [1]

| Run No. | Wt. Ratio CH₂Cl₂/(CH₃CH₂)₂O | Wt. Ratio Solvent/Reactants | Chloroaminododecane Yield, % of Theory |
|---|---|---|---|
| 2 | 6/1 | 4.3 | 20.8 |
| 8 | 3.5/1 | 4.7 | 16.9 |
| 9 | 0 | 1.8 | 8.15 |

[1]Mole ratio of NH₂Cl/AlCl₃/1-dodecane = 0.4/1/2 in above

TABLE IV
EFFECT OF REACTION TIME ON CHLOROAMINODODECANE YIELD [1]

| Run No. | Reaction Time, Hrs. | Mole Ratios NH₂Cl/AlCl₃/1-dodecane | Chloroamino-dodecane Yield Wt.% of Theory |
|---|---|---|---|
| 2 | 1 | 0.04 / 1 / 2 | 20.8 |
| 10 | 3 | 0.03 / 1 / 2 | 26.0 |

[1]Weight ratio CH₂Cl₂/(CH₃CH₂)₂O = 6:1 in both runs

As the several illustrative examples indicate and the disclosure documents, numerous advantages are available to the practitioner of the novel process of this invention.

For example, the addition of monochloroamine to alpha-olefins in the presence of aluminum chloride catalyst at atmospheric pressure and below 0° C gives much better results than those reported in the known prior art. Further, the uncatalyzed additions under more stringent "forcing" conditions of higher temperatures and autogenous pressures, result in much smaller yields of chloraminoalkane products having vicinal amino and chloro groups on adjacent carbon atoms which employ aluminum chloride catalyst. Similarly while the yields obtained through the addition of N,N-dialkyl chloroamines to the alpha-olefins does not produce the tertiary amines in good yields, higher yields may be obtained by the adjustment of reaction parameters in a manner similar to that described for monochloroamine.

Other advantages will be more readily gleaned by those skilled in the art after reviewing the claims in light of the specification.

What is claimed is:

1. A process for preparing alkyl amines possessing vicinal chlorine and an amino group which comprises:
   (a) forming a chilled reaction mixture solution of alpha olefins containing from 4 to 20 carbon atoms and a chloroamine selected from the group consisting of monochloramine and N-alkylchloroamines, in the presence of a polychlorinated dispersing inert solvent and an aluminum chloride catalyst;
   (b) maintaining the chilled reaction mixture at about $-50°$ to $-10°$ C for 1 to 3 hours, washing the organic layer with diluted HCl to remove catalyst residues and separating the organic layer rich in product from the water layer.

2. The process of claim 1 wherein the 1-olein is a mixture containing 8 to 20 carbon atoms.

3. The process of claim 1 wherein the chloroamine is a N-alkylchloroamine.

4. The process of claim 1 wherein the alpha olefin is 1-tetradecene.

5. The process of claim 1 wherein the 1-olefin is 1-dodecene.

* * * * *